(12) United States Patent
Arnett et al.

(10) Patent No.: US 11,759,190 B2
(45) Date of Patent: Sep. 19, 2023

(54) LOCK FOR MEDICAL DEVICES, AND RELATED SYSTEMS AND METHODS

(71) Applicant: Boston Scientific Medical Device Limited, Galway (IE)

(72) Inventors: Jeffery Arnett, Gilbert, AR (US); Gareth Davies, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 307 days.

(21) Appl. No.: 17/070,442

(22) Filed: Oct. 14, 2020

(65) Prior Publication Data

US 2021/0113198 A1 Apr. 22, 2021

Related U.S. Application Data

(60) Provisional application No. 62/923,051, filed on Oct. 18, 2019.

(51) Int. Cl.
*A61B 17/00* (2006.01)
*A61B 17/34* (2006.01)

(52) U.S. Cl.
CPC ...... *A61B 17/0057* (2013.01); *A61B 17/3417* (2013.01); *A61B 2017/00584* (2013.01); *A61B 2017/00619* (2013.01)

(58) Field of Classification Search
CPC ............ A61B 17/0057; A61B 17/3417; A61B 17/3478; A61B 17/3494; A61B 2017/00243; A61B 2017/0046; A61B 2017/00469; A61B 2017/00584; A61B 2017/00619; A61B 2090/034; A61B 2090/035; A61B 2090/08021
See application file for complete search history.

(56) References Cited

U.S. PATENT DOCUMENTS

| 175,254 | A | 3/1876 | Oberly |
|---|---|---|---|
| 827,626 | A | 7/1906 | Gillet |
| 848,711 | A | 4/1907 | Weaver |
| 1,072,954 | A | 9/1913 | Junn |
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |

(Continued)

*Primary Examiner* — Mohamed G Gabr
(74) *Attorney, Agent, or Firm* — Nelson Mullins Riley & Scarborough

(57) ABSTRACT

A lock for positioning a first medical device with respect to a second medical device includes a spacer for preventing advancement of the first medical device towards the second medical device. The spacer is movable between a lock position and an unlock position. In the lock position, the spacer is moved transverse to the longitudinal axis with respect to the unlock position. The lock further includes a rotary stop integral with the spacer for fixing the rotational position of the first medical device with respect to the second medical device. The lock further includes a clip integral with the spacer and removably securable to the first medical device in a first position to secure the spacer in the unlock position, and removably securable to the first medical device in a second position to secure the spacer in the lock position.

19 Claims, 10 Drawing Sheets

(56) References Cited

U.S. PATENT DOCUMENTS

| | | |
|---|---|---|
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,966,587 A * | 10/1990 | Baumgart ........... A61B 17/3417 604/164.09 |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,222,974 A * | 6/1993 | Kensey ............... A61B 17/0057 604/15 |
| 5,230,349 A | 7/1993 | Langberg |
| 5,242,410 A * | 9/1993 | Melker ................. A61M 25/06 604/164.1 |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Undquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |

(56) References Cited

U.S. PATENT DOCUMENTS

| | | |
|---|---|---|
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |

(56) References Cited

U.S. PATENT DOCUMENTS

2019/0021763 A1    1/2019   Zhou et al.
2019/0247035 A1    8/2019   Gittard et al.

\* cited by examiner

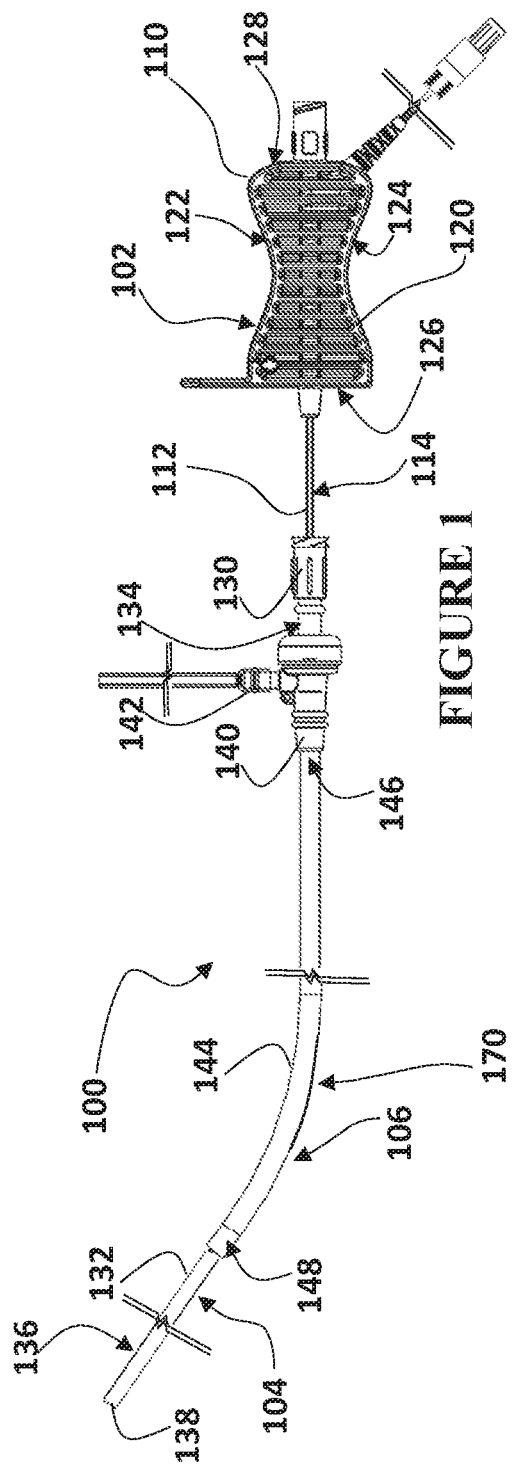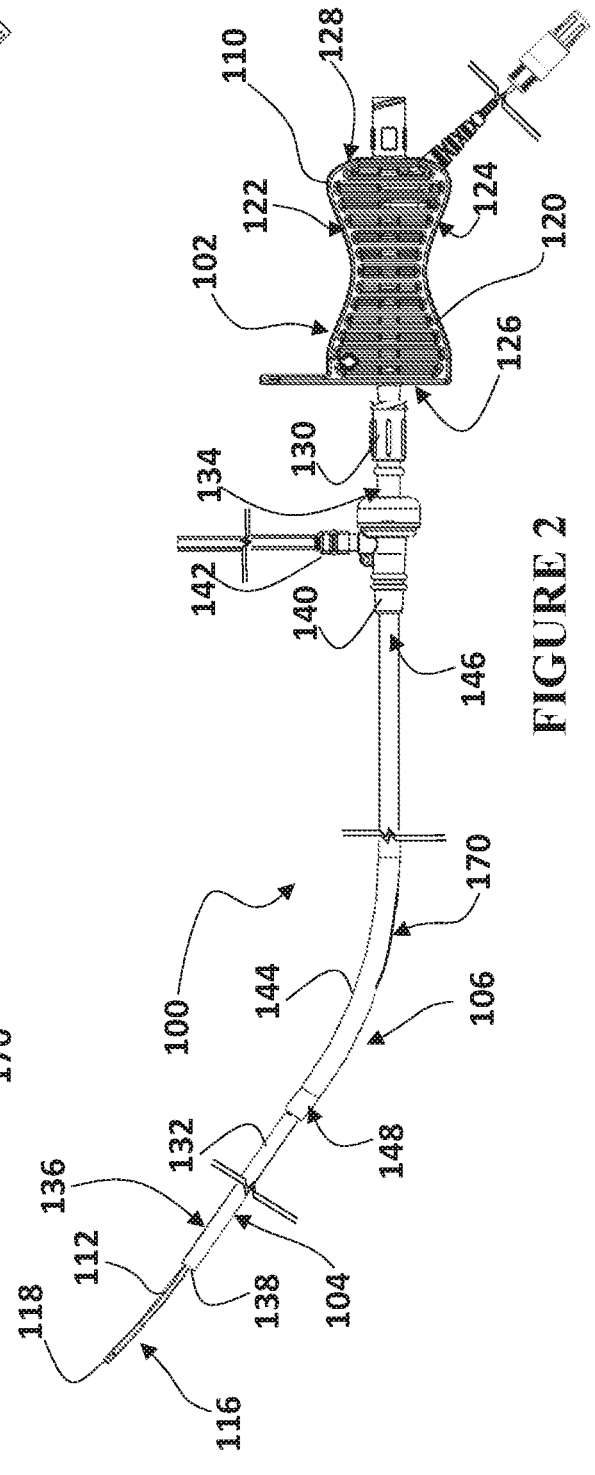

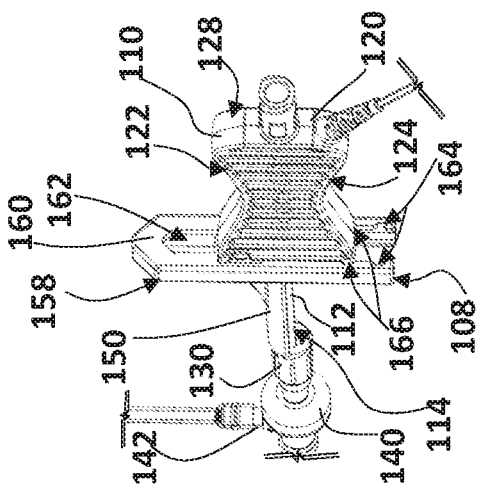
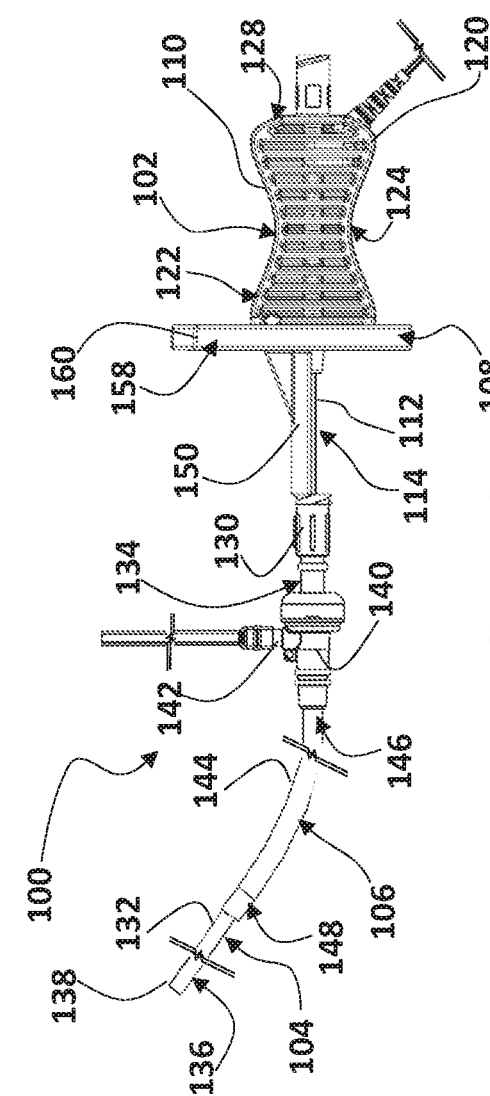
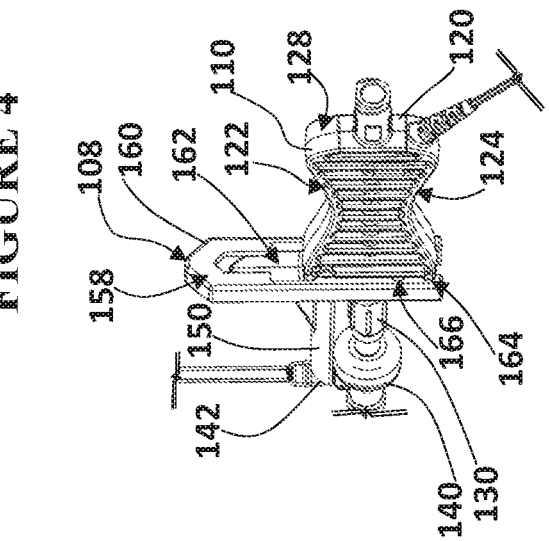
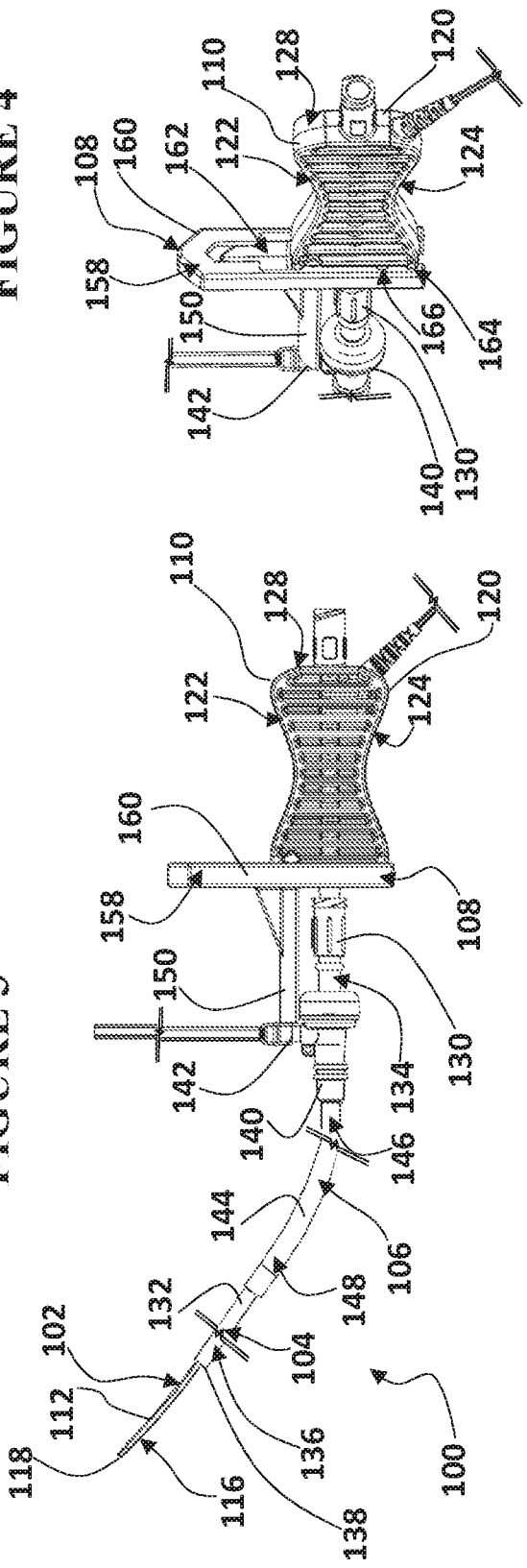

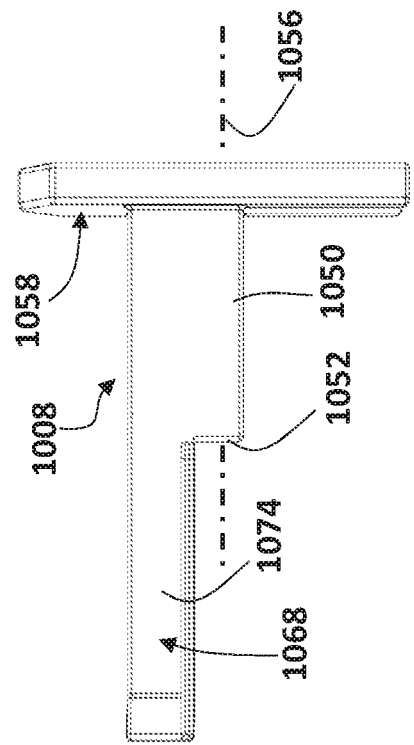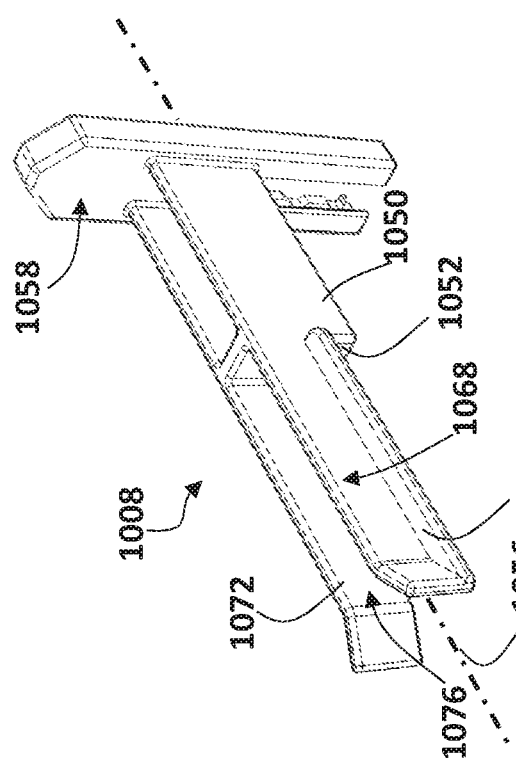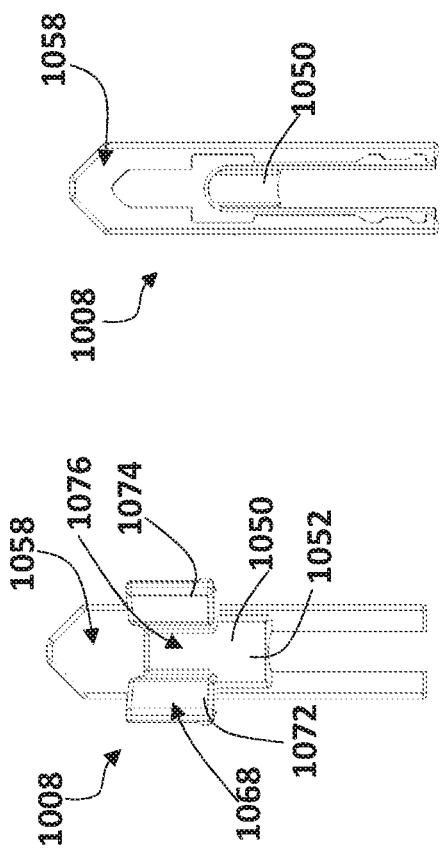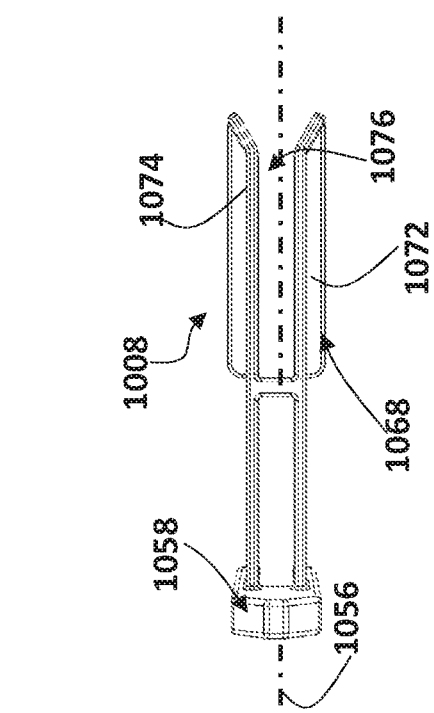
FIGURE 10
FIGURE 11
FIGURE 12
FIGURE 13
FIGURE 14

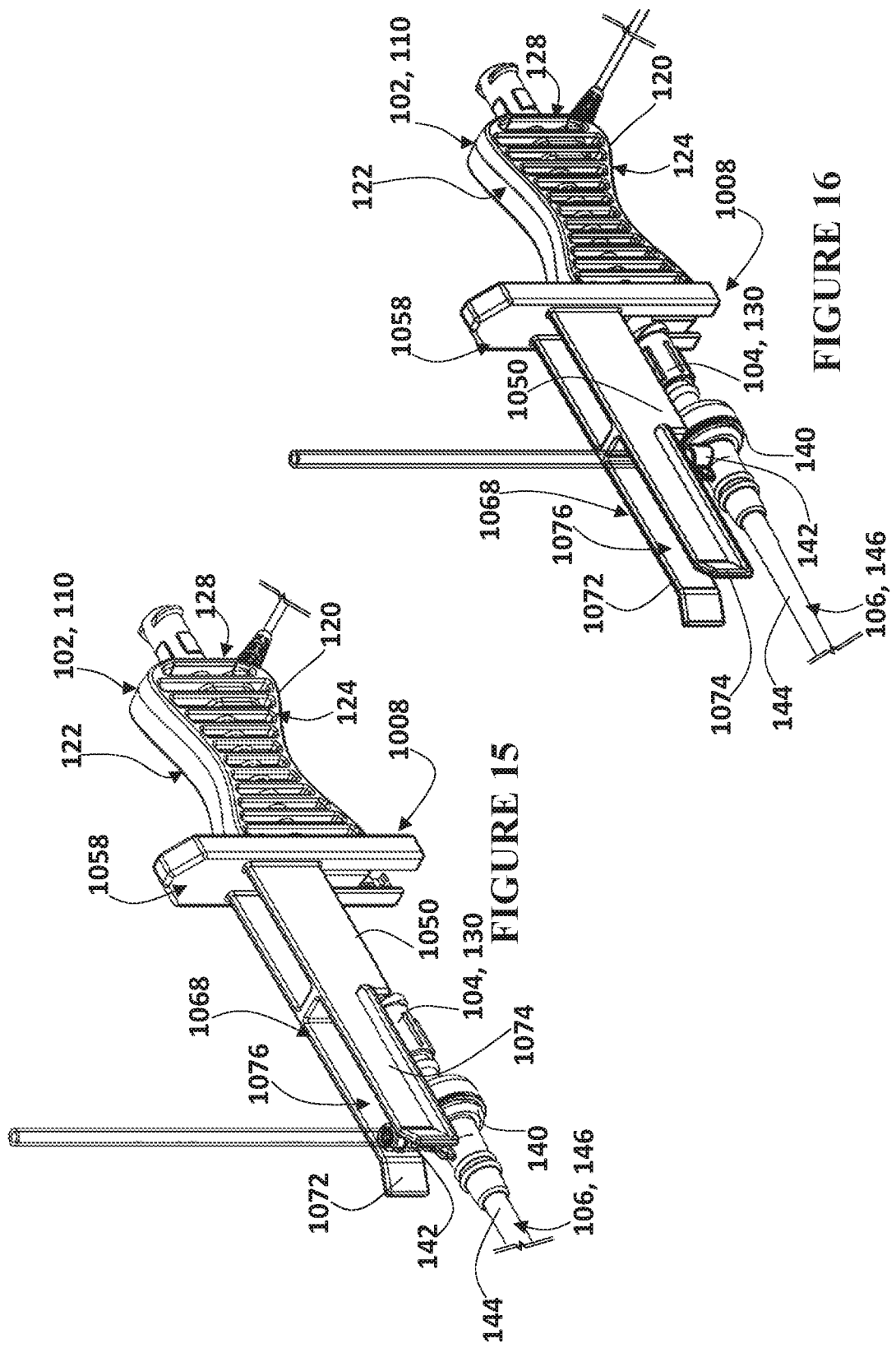

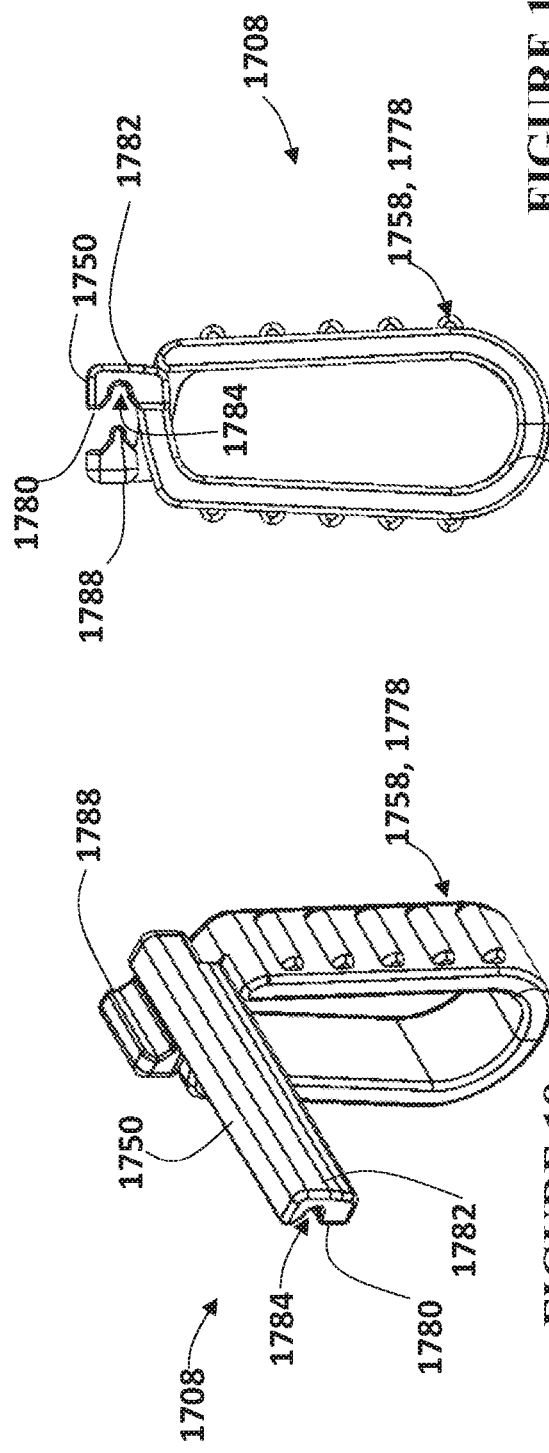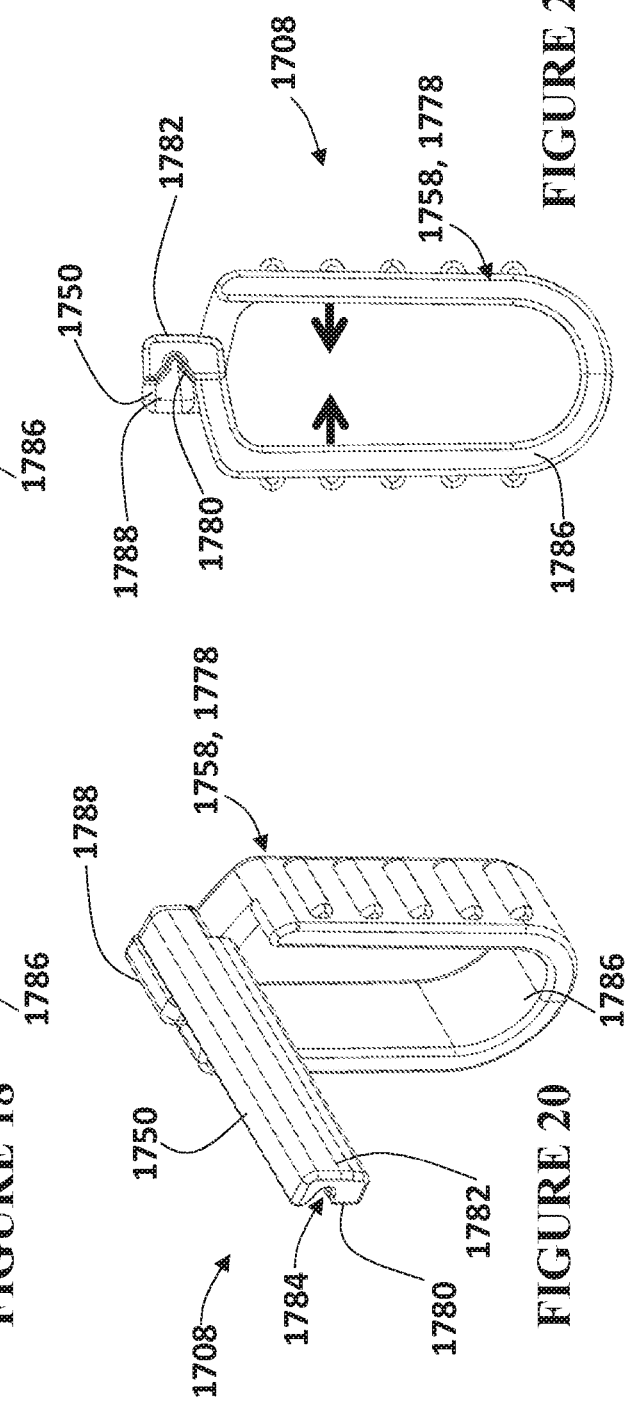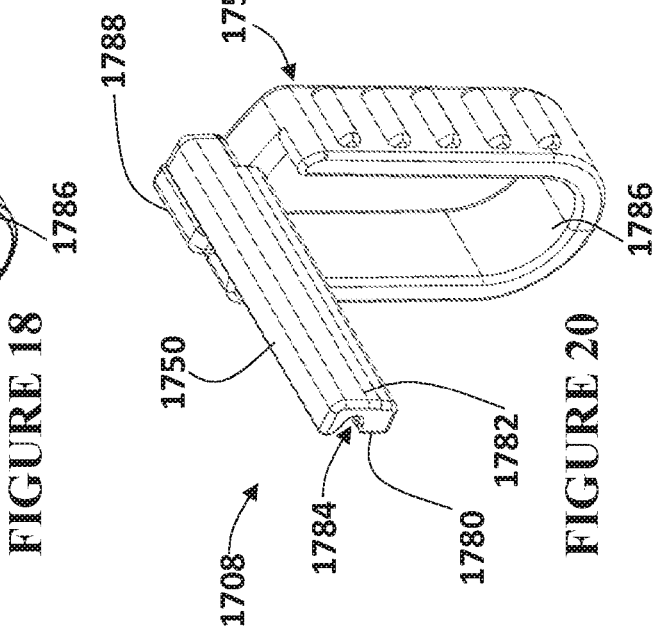

LOCK FOR MEDICAL DEVICES, AND RELATED SYSTEMS AND METHODS

FIELD

This document relates to locks for medical devices. More specifically, this document relates to locks for maintaining the position of medical devices with respect to each other, and related systems and methods.

SUMMARY

The following summary is intended to introduce the reader to various aspects of the detailed description, but not to define or delimit any invention.

A kit of parts for a system for transseptal perforation is disclosed. According to some aspects, the kit of parts includes a first medical device. The first medical device has a first medical device proximal end and a first medical device distal tip. The kit further includes a second medical device has a second medical device proximal and a second medical device distal tip. The second medical device proximal end comprises a hub. The first medical device is receivable and advanceable through the second medical device from the hub towards the second medical device distal tip to a shrouded position in which the first medical device distal tip is shrouded within the second medical device, and to an in-use position in which the first medical device distal tip is proud of the second medical device distal tip. The kit further includes a lock for releasably preventing advancement of the first medical device from the shrouded position to the in-use position. The lock includes an elongate spacer positionable in a lock position proximal of the hub to abut the hub and prevent movement of the first medical device to the in-use position, and a clip for securing the lock to the first medical device with the spacer in the lock position.

In some examples, the first medical device is a transseptal perforation device. The transseptal perforation device includes an elongate needle. The second medical device comprises a dilator with a dilator hub and elongate dilator body.

In some examples, the transseptal perforation device includes a handle, and the needle proximal end is secured to the handle. In the shrouded position, the handle can be spaced from the dilator hub, and in the in-use position, the handle can be moved towards the dilator hub. In the lock position, the spacer can be positioned between the dilator hub and the handle to abut the dilator hub and the handle and prevent movement of the handle towards the dilator hub.

In some examples, the spacer is movable from the lock position to an unlock position. In the unlock position, the spacer is moved clear of the dilator hub to allow movement of the handle towards the dilator hub and allow movement of the needle to the in-use position. The spacer can be securable in the unlock position by the clip.

In some examples, the clip includes a tongue extending orthogonally from the spacer and defining a slot for receiving at least a portion of the handle. In some examples, the handle includes a rib, and the tongue includes a first detent engageable with the rib to maintain the spacer in the unlock position, and a second detent spaced from the first detent and engageable with the rib to maintain the spacer in the lock position.

In some examples, the clip is slidable in a direction transverse to a longitudinal axis of the spacer, to move the spacer between the lock position and the unlock position.

In some examples, the lock further includes a rotary stop for fixing the rotational position of the first medical device.

In some examples, the rotary stop fixes the rotational position of the first medical device relative to the second medical device.

In some examples, the kit further includes a sheath having a sheath hub including a radially extending fluid port, an elongate sheath body extending longitudinally from the sheath hub and having a sheath body proximal end adjacent the sheath hub and a sheath body distal end spaced from the sheath hub, and a sheath lumen extending longitudinally through the sheath from the sheath hub to the sheath body distal end. The dilator body can be advanced through the sheath lumen to position the dilator body within the sheath body with the dilator hub adjacent the sheath hub and the dilating tip proud of the sheath body distal end. The clip can further include a rotary stop for releasably fixing the rotational position of the transseptal perforation device with respect to the sheath. The rotary stop can include a pair of arms defining a space therebetween for receiving a curved indicator.

In some examples, the curve indicator comprises a fluid port.

In some examples, the kit further includes a sensor for detecting when the spacer is in the lock position.

A lock for positioning a first medical device with respect to a second medical device is also disclosed. According to some aspects, the lock includes a spacer for allowing partial advancement of the first medical device towards the second medical device. The spacer is elongate and has a first abutment surface and a second abutment surface spaced apart along a longitudinal axis of the spacer. The spacer is movable between a lock position and an unlock position. In the lock position, the spacer is moved transverse to the longitudinal axis with respect to the unlock position. The lock further includes a rotary stop integral with the spacer for fixing the rotational position of the first medical device with respect to the second medical device. The rotary stop includes a pair of arms offset from the longitudinal axis and defining a space therebetween for receiving a portion of the second medical device. The lock further includes a clip integral with the spacer and removably securable to the first medical device in a first position to secure the spacer in the unlock position, and removably securable to the first medical device in a second position to secure the spacer in the lock position.

In some examples, the arms extend distally beyond the first abutment surface of the spacer.

In some examples, the arms are positioned to receive the portion of the second medical device when the spacer is in the lock position and when the spacer is in the unlock position.

In some examples, the clip includes a tongue extending orthogonally from the spacer and defining a slot for receiving a portion of the first medical device. In some examples, the tongue includes a first detent engageable with the portion of the first medical device to secure the spacer in the unlock position, and a second detent spaced from the first detent and engageable with the portion of the first medical device to maintain the spacer in the lock position.

In some examples, the clip is slidable transverse to the longitudinal axis between the first position and the second position.

Another lock for positioning a first medical device with respect to a second medical device is also disclosed. The lock includes a spacer for allowing partial advancement of the first medical device towards the second medical device.

The spacer is elongate and has a first abutment surface and a second abutment surface spaced apart along a longitudinal axis of the spacer. The spacer is movable between a lock position and an unlock position. In the lock position the spacer is moved transverse to the longitudinal axis with respect to the unlock position. A clip is integral with the spacer and is removably securable to the first medical device in a first position to secure the spacer in the unlock position, and removably securable to the first medical device in a second position to secure the spacer in the lock position. The clip includes a tongue extending orthogonally from the spacer and defining a slot for receiving a portion of the first medical device. The tongue includes a first detent engageable with the portion of the first medical device to secure the spacer in the unlock position, and a second detent spaced from the first detent and engageable with the portion of the first medical device to maintain the spacer in the lock position.

In some examples, the clip is slidable transverse to the longitudinal axis between the first position and the second position.

In some examples, the lock further includes a rotary stop integral with the spacer for fixing the rotational position of the first medical device with respect to the second medical device. The rotary stop can include a pair of arms offset from the longitudinal axis and defining a space therebetween for receiving a portion of the second medical device. The arms can extend distally beyond the first abutment surface of the spacer. The arms can be positioned to receive the portion of the second medical device when the spacer is in the lock position and when the spacer is in the unlock position.

Another kit of parts for a system for transseptal perforation is disclosed. According to some aspects, the kit of parts includes a transseptal perforation device including an elongate needle. The needle has a needle proximal end and a needle distal end including a perforating tip. The kit further includes a dilator including a dilator hub and an elongate dilator body having a dilator lumen extending therethrough. The dilator body has a dilator body proximal end secured to the dilator hub and a dilator body distal end including a dilating tip. The needle is advanceable through the dilator from the dilator hub towards the dilating tip to a shrouded position in which the perforating tip is shrouded within the dilator, and to an in-use position in which the perforating tip is proud of the dilating tip. The kit further includes a lock for releasably preventing advancement of the needle from the shrouded position to the in-use position. The lock includes an elongate spacer positionable in a lock position proximal of the dilator hub to abut the dilator hub and prevent movement of the needle to the in-use position, and a clip for securing the lock to the transseptal perforation device with the spacer in the lock position.

A method for carrying out a cardiac procedure is also disclosed. According to some aspects, the method includes a. securing a lock to a transseptal perforation device and positioning a spacer of the lock in a lock position; b. with the lock in the lock position, advancing the transseptal perforation device into a dilator having a dilator hub, whereby when in the lock position, the spacer is positioned proximal of the dilator hub to abut the dilator hub and limit advancement of the transseptal perforation device into the dilator and thereby prevent advancement of a perforating tip of the transseptal perforation device proud of a dilating tip of the dilator; c. positioning the dilating tip adjacent a target location in a patient's heart; d. removing the spacer from the lock position to clear the spacer of the dilator hub; e. advancing the transseptal perforation device further into the dilator to position the perforating tip proud of the dilating tip; and f. using the perforating tip to perforate the target location.

In some examples, step a. includes engaging a clip of the lock with a handle of the transseptal perforation device. In some examples, step a. includes engaging a first detent of the clip with a rib of the handle to secure the lock to the transseptal perforation device with the spacer in an unlock position, snapping the first detent out of engagement with the rib and sliding the clip along the handle, and snapping a second detent of the clip into engagement with the rib of the handle to position the spacer of the lock in the lock position.

In some examples, step d. includes moving the spacer from the lock position to an unlock position, whereby in the unlock position, the clip is secured to the transseptal perforation device with the spacer clear of the hub of the dilator. In some examples, moving the spacer from the lock position to the unlock position further includes snapping a second detent of the clip out of engagement with a rib of the handle, sliding the clip along the handle, and snapping a first detent of the clip into engagement with the rib of the handle.

In some examples, the method further includes, prior to step c., advancing the dilator into a sheath having a sheath hub to position the dilator hub adjacent the sheath hub. Step b. can include engaging a rotary stop of the lock with the sheath hub to fix the rotational position of the transseptal perforation device with respect to the sheath. In some examples, the method includes maintaining the engagement of the rotary stop and the sheath hub during steps d. and e.

In some examples, the method includes using a sensor to detect when the spacer is in the lock position, and automatically preventing energizing of the transseptal perforation device when the sensor detects that the spacer is in the lock position.

BRIEF DESCRIPTION OF THE DRAWINGS

The accompanying drawings are for illustrating examples of articles, methods, and apparatuses of the present disclosure and are not intended to be limiting. In the drawings:

FIG. 1 is a side view of an example system for transseptal perforation, with a needle of the system in a shrouded position, and with a lock of the system not shown;

FIG. 2 is a side view of the system of FIG. 1, with the needle of the system in an in-use position, and with the lock of the system not shown;

FIG. 3 is a side view of the system of FIG. 1, with the needle of the system in the shrouded position, and with the lock of the system shown;

FIG. 4 is partial perspective view of the system of FIG. 1, with the needle of the system in the shrouded position, and with the lock of the system shown;

FIG. 5 is a side view of the system of FIG. 1, with the needle of the system in the in-use position, and with the lock of the system shown;

FIG. 6 is a partial perspective view of the system of FIG. 1, with the needle of the system in the in-use position, and with the lock of the system shown;

FIG. 10 is a perspective view of another example lock;
FIG. 11 is a side view of the lock of FIG. 10;
FIG. 12 is a top view of the lock of FIG. 10;
FIG. 13 is a front view of the lock of FIG. 10;
FIG. 14 is a rear view of the lock of FIG. 10;

FIG. 15 is a partial perspective view of another system for transseptal perforation, showing a needle of the system in a shrouded position, and including the lock of FIGS. 10 to 14;

FIG. 16 is a partial perspective view of the system for transseptal perforation of FIG. 15, showing the needle of the system in an in-use position, and including the lock of FIGS. 10 to 15;

FIG. 18 is a perspective view of the lock of FIG. 17, with the lock in a released state;

FIG. 19 is a front view of the lock of FIG. 17, with the lock in the released state;

FIG. 20 is a perspective view of the lock of FIG. 17, with the lock in a clamped state; and FIG. 21 is a perspective view of the lock of FIG. 17, with the lock in the clamped state.

DETAILED DESCRIPTION

Figure 8:
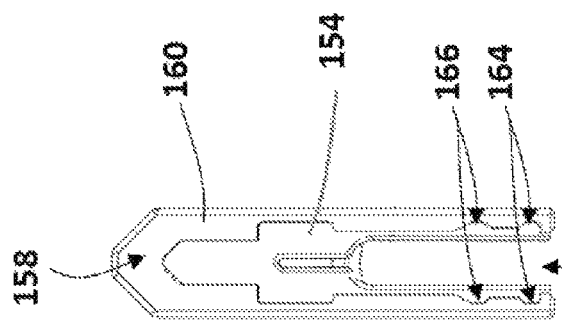
FIG. 8 is a rear view of the lock of FIGS. 3 to 6.

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are locks for medical devices. More specifically, disclosed herein are various examples of a lock that can be used to maintain the position a first medical device with respect to a second medical device, or to facilitate the positioning of a first medical device with respect to a second medical device, to facilitate ease of use and enhance patient safety. In some examples, the locks disclosed herein can be used as part of a system for transseptal perforation, which can further include a dilator, a sheath, and a transseptal perforation device. During use of such systems, the sheath can be advanced to the right atrium of a patient's heart via the femoral vein and positioned adjacent a target location in the right atrium, for example the fossa ovalis of the atrial septum. The transseptal perforation device (e.g. a radiofrequency (RF) perforation device) and dilator can then be guided through the sheath, to the right atrium, with a perforating tip of the transseptal perforation device shrouded in the dilator during advancement. When the operator of the system is ready (e.g. after various tests have been carried out and/or when all devices are confirmed to be in the desired position), the transseptal perforation device can be advanced out of the dilator and used to create a perforation in the target location. The dilator can then be advanced through the perforation to dilate the perforation. Such procedures can be carried out, for example, as a medical treatment, or to gain access to the left atrium for a subsequent medical treatment. In such systems, as will be described further detail below, the locks as disclosed herein can be used to prevent the perforating tip of the transseptal perforation device from being prematurely advanced out of the dilator. That is, the locks as described herein can maintain the perforating tip shrouded within the dilator until the operator of the system is ready to advance the transseptal perforation device out of the dilator. Furthermore, the locks as described herein can fix the rotational position of the transseptal perforation device with respect to the sheath and/or dilator, to facilitate curving of the transseptal perforation device in a desired direction, so that upon advancement, the transseptal perforation device is advanced towards the target location.

Referring now to FIGS. 1 to 6, an example system 100 for transseptal perforation is shown. The system 100 includes a transseptal perforation device 102, a dilator 104, a sheath 106, and a lock 108. For ease of understanding, the system 100 is shown without the lock 108 in FIGS. 1 and 2, and with the lock 108 in FIGS. 3 to 6. In alternative examples (not shown), the sheath may be omitted, and a dilator may serve as both a sheath and a dilator. Such dilators are sold by Baylis Medical Company Inc. (Montreal, Canada) under the brand name ExpanSure™ Transseptal Dilation System.

Referring to FIGS. 1 and 2, in the example shown, the transseptal perforation device 102 has a handle 110 and an elongate needle 112, which is generally flexible. The needle 112 has a needle proximal end 114 (shown in FIG. 1) secured to the handle 110 and a needle distal end 116 including a perforating tip 118 (shown in FIG. 2). The perforating tip 118 can be, for example, a radiofrequency perforating tip, or a mechanical perforating tip. The handle 110 includes several ribs, including an outer rib 120 extending around the perimeter of the handle 110. The outer rib 120 includes an upper section 122, a lower section 124, a front section 126, and a rear section 128.

Referring still to FIGS. 1 and 2, the 104 dilator has a dilator hub 130, and an elongate dilator body 132. The dilator body 132 has a dilator lumen (not shown) extending therethrough, a dilator body proximal end 134 secured to the dilator hub 130 and a dilator body distal end 136 including a dilating tip 138.

Referring still to FIGS. 1 and 2, the sheath 106 has a sheath hub 140 including a radially extending fluid port 142, and an elongate sheath body 144 extending longitudinally from the sheath hub 140. In some embodiments, the fluid port 142 may be indicative of the direction of curvature of the sheath 106. In alternative embodiments, the fluid port 142 may be replaced by a curve indicator (not shown). The sheath body 144 has a sheath body proximal end 146 adjacent the sheath hub 140, and a sheath body distal end 148 spaced from the sheath hub 140. A sheath lumen (not shown) extends longitudinally through the sheath from the sheath hub 140 to the sheath body distal end 148.

In use, as shown in FIGS. 1 and 2, the dilator body 132 is advanceable through the sheath lumen to position the dilator body 132 within the sheath body 144, with the dilator hub 130 adjacent the sheath hub 140 and the dilating tip 138 proud of the sheath body distal end 148. Furthermore, the needle 112 of the transseptal perforation device 102 is advanceable through the dilator 104 to a shrouded position, shown in FIG. 1, in which the perforating tip 118 (not visible in FIG. 1) is shrouded within the dilator 104 and the handle 110 is spaced from the dilator hub 130, to an in-use position, shown in FIG. 2, in which the perforating tip 118 is proud of the dilating tip 138 and the handle 110 is adjacent the dilator hub 130 (e.g. the handle 110 can abut the dilator hub 130). When the needle 112 is in the shrouded position, the patient's anatomy is protected from contact with the perforating tip 118, as the perforating tip is shrouded within the dilator 104. When the needle 112 is in the in-use position, the perforating tip 118 is exposed, and can perforate anatomical structures.

Referring now to FIGS. 3 to 6, the system 100 is shown with the lock 108. The lock 108 can be used to prevent advancement of the needle 112 from the shrouded position (shown in FIGS. 3 and 4) to the in-use position (shown in FIGS. 4 and 5), until such advancement is desired by the operator. For example, the lock 108 can be used up until the operator of the system is ready to perforate a target location within a patient's heart, for example during advancement of the dilator 104 and transseptal perforation device 102 through the sheath 106 towards the target location, and during any preliminary tests, in order to prevent inadvertent contact between the perforating tip 118 and non-target locations within a patient's body, and prevent inadvertent damage to such non-target locations.

Figure 9:
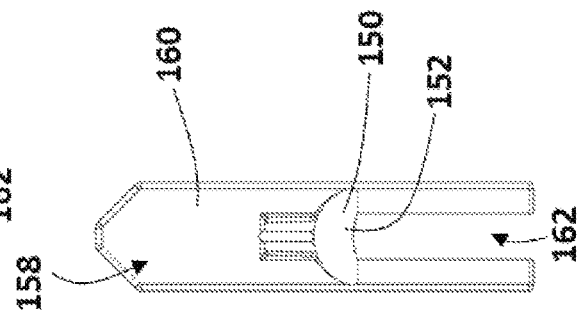
FIG. 9 is a front view of the lock of FIGS. 3 to 6.
Figure 7:
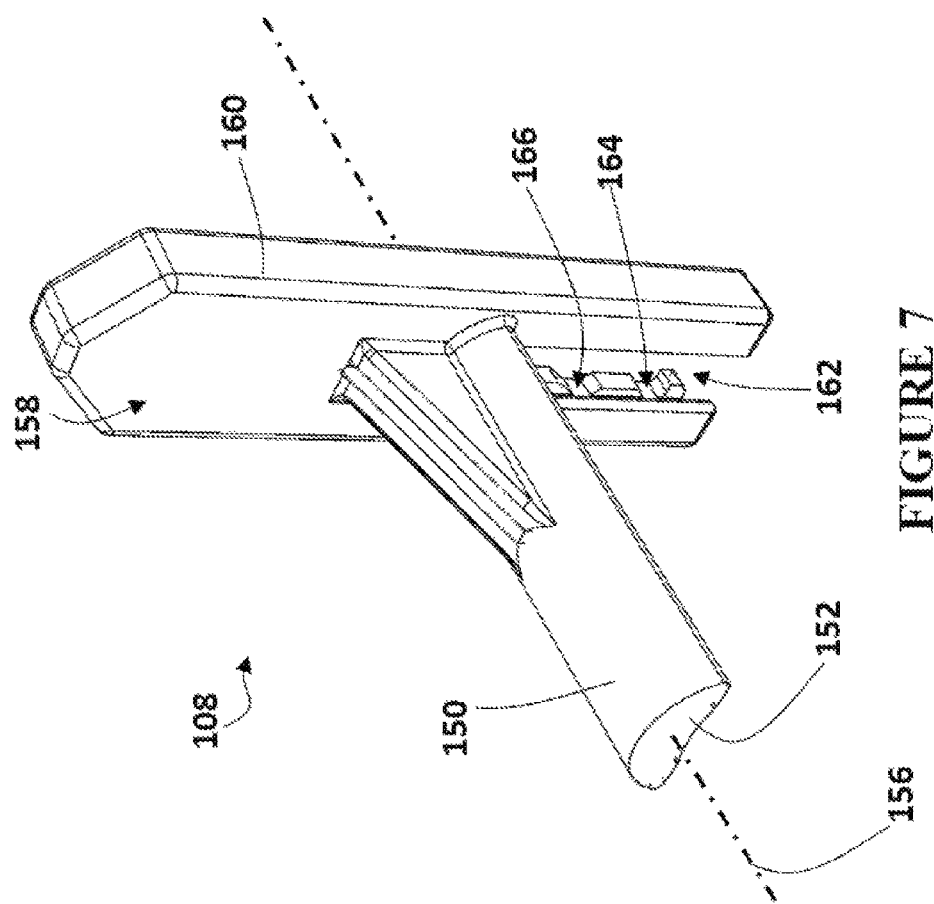
FIG. 7 is a perspective view of the lock of FIGS. 3 to 6.

Referring now to FIGS. 7 to 9, the lock 108 will be described in greater detail. In the example shown, the lock 108 includes an elongate spacer 150. The spacer 150 has a first abutment surface 152 (visible in FIGS. 7 and 9) and a second abutment surface 154 (visible in FIG. 8) spaced apart along a longitudinal axis 156 of the spacer 150. The lock 108 further includes a clip 158, which is integral with the spacer 150. The clip 158 includes a tongue 160 that extends orthogonally from the spacer 150, and defines a slot 162. The tongue 160 further includes a first detent 164 and a second detent 166 spaced apart from the first detent 164.

In use, the clip 158 can snap onto the handle 110 of the transseptal perforation device 102, to position the spacer 150 proximal of the dilator hub 130, and between the dilator hub 130 and the handle 110, so that if advancement of the needle 112 beyond the shrouded position is attempted (e.g. inadvertently), the spacer 150 will abut the dilator hub 130 to prevent movement of the needle 112 to the in-use position by preventing movement of the handle 110 towards the dilator hub 130. More specifically, referring to FIGS. 3 and 4, the lock 108 is shown with the spacer 150 in a lock position. In the lock position, the spacer 150 is proximal of the dilator hub 130, and between the dilator hub 130 and the handle 110, to abut the dilator hub 130 (and also the handle 110) if movement of the handle 110 towards the dilator hub 130 is attempted. This abutment prevents movement of the needle 112 to the in-use position, by preventing movement of the handle 110 towards the dilator hub 130.

Referring to FIGS. 5 and 6, the lock 108 is shown with the spacer 150 in an unlock position. In the unlock position, the spacer 150 is moved radially away from the dilator hub 130 and the handle 110, in a direction transverse to the longitudinal axis 156 of the spacer 150, so that the spacer 150 is clear of the dilator hub 130, to allow movement of the handle 110 towards the dilator hub 130 and therefore allow movement of the needle 112 to the in-use position.

Referring still to FIGS. 3 to 6, the clip 158 serves to secure the lock 108 to the transseptal perforation device. In the example shown, the clip 158 secures the lock 108 to the handle 110 with the spacer 150 in the lock position, and secures the lock 108 to the handle 110 with the spacer in the unlock position, and allows for movement of the spacer 150 between the lock and unlock positions. That is, the clip 158 is removably securable to the handle 110 in a first position, shown in FIGS. 5 and 6, to secure the spacer 150 in the unlock position, and removably securable to the handle 110 in a second position, shown in FIGS. 3 and 4 to secure the spacer 150 in the lock position. More specifically, the slot 162 (shown in FIGS. 7 to 9) of the clip 158 can receive the handle 110, particularly the front section 126 (shown in FIGS. 1 and 2) of the outer rib 120 of the handle 110, which can slide into the slot 162 going in a direction transverse to the longitudinal axis 156 of the spacer 150, from the upper section 122 of the outer rib 120 towards the lower section 124 of the outer rib 120. During sliding of the front section 126 into the slot 162, as the lower section 124 approaches the first detent 164, the lower section 124 will engage the first detent 164 by snapping into the first detent 164. When the lower section 124 is engaged with the first detent 164, the spacer 150 is secured in the unlock position, as shown in FIGS. 5 and 6. If further force is applied to slide the front section 126 further into the slot 162, the lower section 124 will snap out of engagement with the first detent 164, and towards the second detent 166. As the lower section 124 approaches the second detent 166, the lower section 124 will engage the second detent 166 by snapping into the second detent 166. When the lower section 124 is engaged with the second detent 166, the spacer 150 is secured in the lock position, as shown in FIGS. 3 and 4. Accordingly, the spacer 150 can be moved between the lock and unlock positions by sliding the clip 158 into and out of engagement with the first detent 164 and second detent 166. The configuration of the clip 158 can advantageously allow for one-handed operation of the lock 108.

An example method of using the lock 108 and system 100 of FIGS. 1 to 9 will now be described. In use, the sheath 106 and dilator 104 can be advanced to the right atrium of a patient's heart via the femoral vein and the dilating tip 138 can be positioned adjacent a target location in the right atrium, for example the fossa ovalis of the atrial septum. Prior to or after advancement of the sheath 106 and dilator 104, the lock 108 can be secured to the transseptal perforation device 102, and the spacer 150 of the lock 108 can be positioned the lock position, as shown in FIGS. 3 and 4. More specifically, the clip 158 can be engaged with the handle 110 of the transseptal perforation device 102, by sliding the front section 126 of the outer rib 120 into the slot 162, and engaging the first detent 164 with the lower section 124 of the outer rib 120, to secure the lock to the transseptal perforation device 102 with the spacer 150 in an unlock position. Force can continue to be applied, to snap the first detent 164 out of engagement with the outer rib 120, and to slide the clip 158 further towards the handle 110, to snap the second detent 166 into engagement with the lower section 124 of the outer rib 120. When the clip 158 is in this position (i.e. the second position), the spacer 150 is in the lock position, as shown in FIGS. 3 and 4. With the spacer 150 in the lock position, the transseptal perforation device 102 can be advanced into the dilator 104. As described above, in the lock position, the spacer 150 is positioned between the dilator hub 130 and the handle 110 of the transseptal perforation device 102, to abut the dilator hub 130 and the handle 110 and limit advancement of the transseptal perforation device 102 into the dilator 104, and thereby prevent advancement of a perforating tip 118 of the transseptal perforation device 102 proud of a dilating tip 138 of the dilator 104, to the in-use position. With the perforating tip 118 shrouded in the dilator 104 and prevented from advancing to the in-use position by the lock 108, various optional procedures can be carried out, including procedures to confirm the position of the dilating tip 138 (e.g. using fluoroscopy). When the operator of the system 100 is ready, the spacer 150 can be removed from the lock position, to clear the spacer 150 of the dilator hub 130. That is, the spacer 150 can be moved from the lock position to the unlock position, by snapping the second detent 166 out of engagement with the lower section 124 of the outer rib 120, sliding the clip 158 along the handle, transversely away from the needle 112, and snapping the first detent 166 into engagement with the lower section 124 of the outer rib 120 (as shown in FIGS. 5 and 6). The transseptal perforation device 102 can then be advanced further into the dilator 104 to position the perforating tip 118 proud of the dilating tip 138, in the in-use position. The perforating tip 118 can then be used to perforate the target anatomy.

Figure 22:
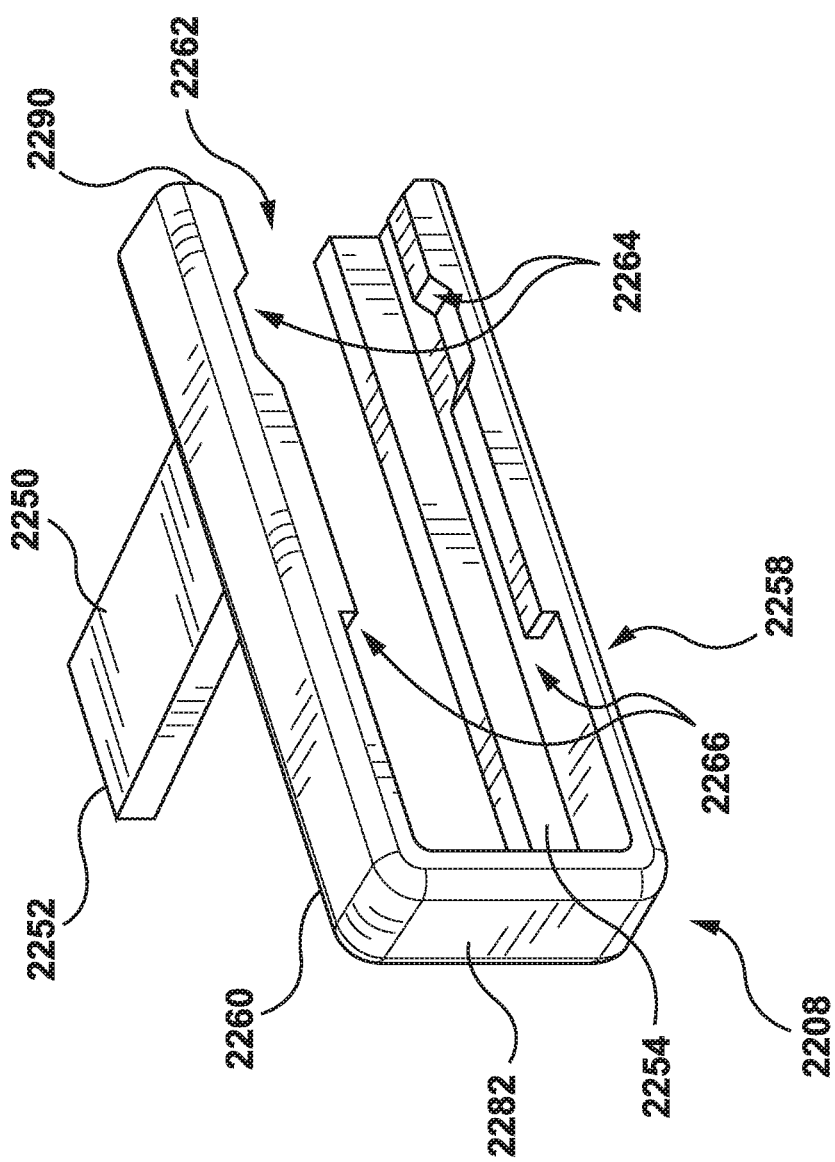
FIG. 22 is a perspective view of another example lock.
Figure 23:
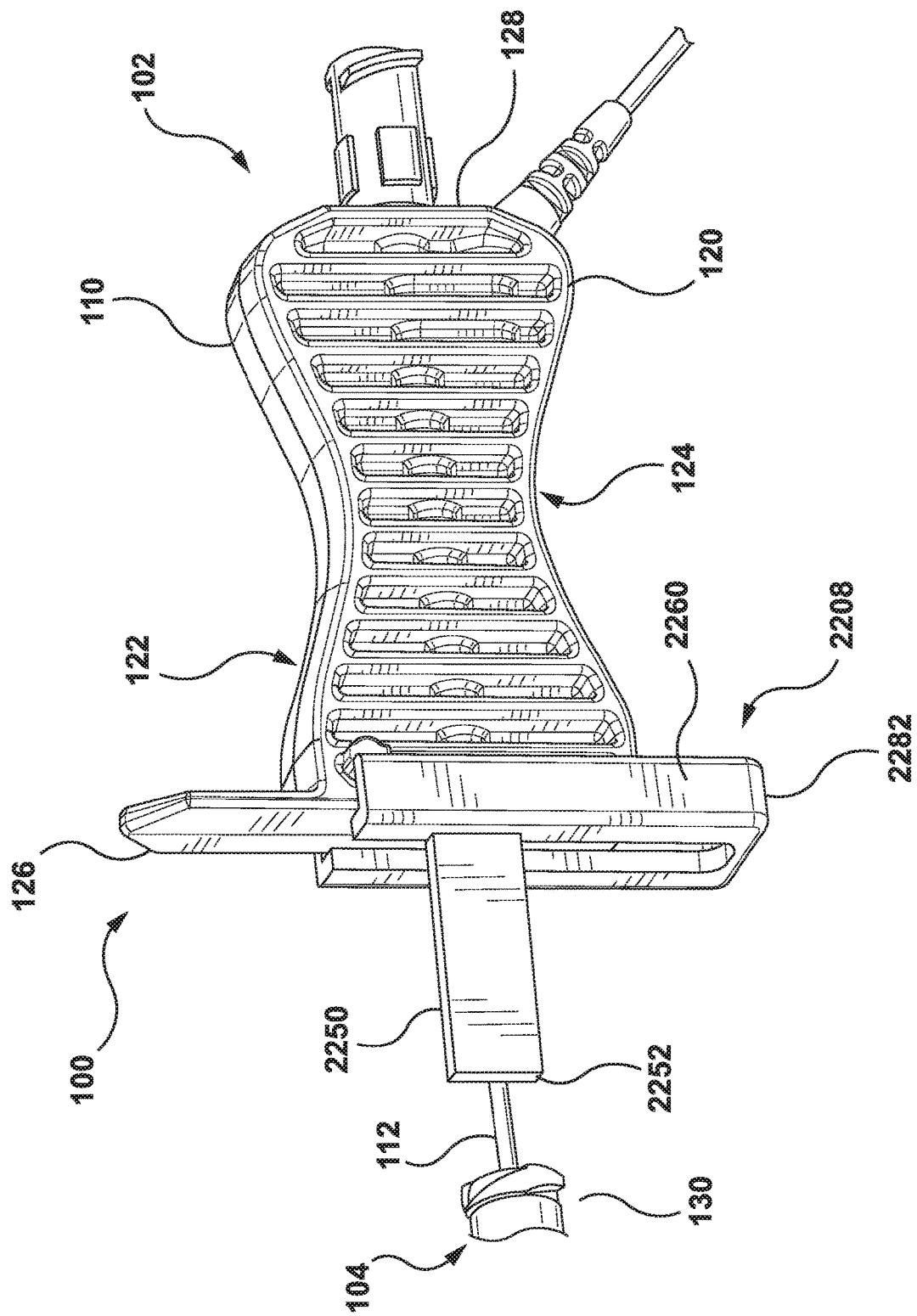
FIG. 23 is a partial perspective view of another system for transseptal perforation including the lock of FIG. 22.
Figure 24:
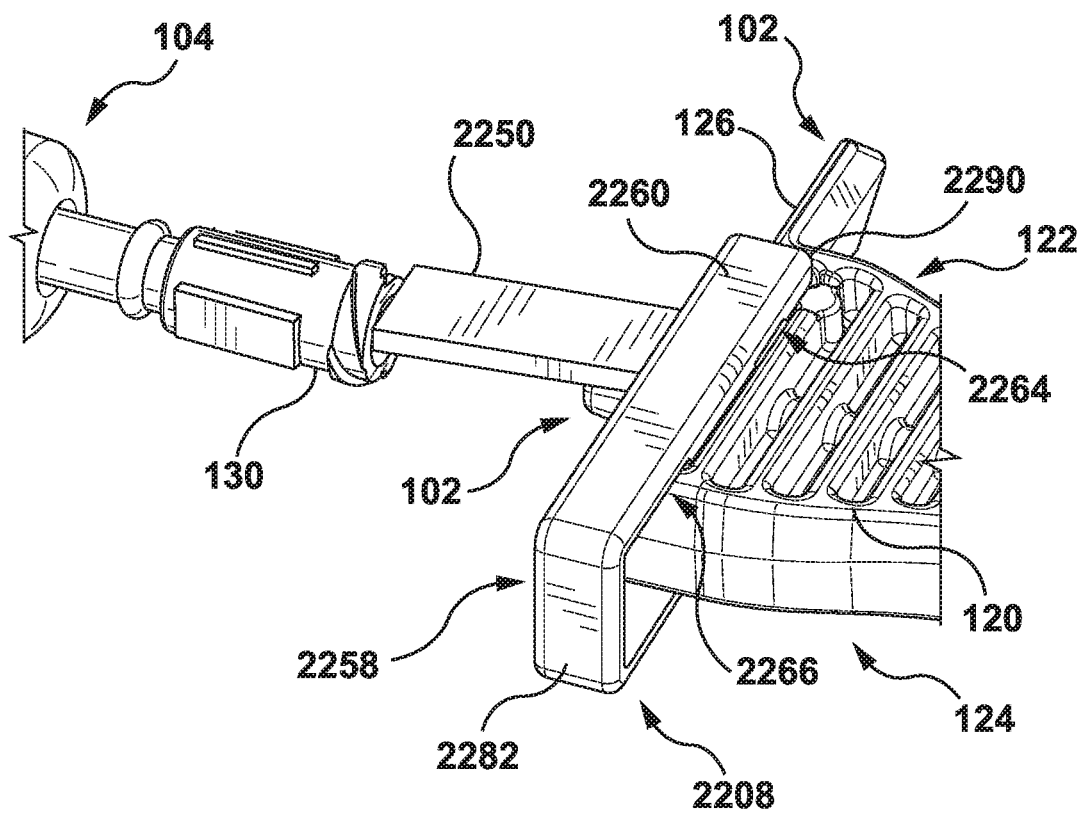
FIG. 24 a partial perspective view of the system for transseptal perforation, showing a needle of the system in a shrouded position, and including the lock of FIG. 22 to 23.

Referring now to FIGS. 22 to 24, another example lock is shown. Features of the lock 2208 that are like features of the lock 108 will be referred to with like reference numerals, incremented by 2100.

Referring now to FIG. 22, the lock 2208 will be described in greater detail. In the example shown, the lock 2208 includes an elongate spacer 2250. The spacer 2250 has a first abutment surface 2252 (visible in FIG. 23) which, in the locked position, contacts the dilator hub 130 (as illustrated in FIG. 24). The lock 2208 further includes a clip 2258, which is integral with the spacer 2250. The clip 2258 includes a tongue 2260 that extends orthogonally from the spacer 2250 and defines a slot 2262. The tongue 2260 further defines a second abutment surface 2254 which provides an abutment surface between the lock 2208 and the handle 110 when positioned on the handle 110. The tongue 2260 further comprises a bottom face 2282 which provides the user with a pushing surface. In some embodiments, the bottom face 2282 may include a smooth finish, providing the user with a better pushing surface during use. The tongue 2260 further includes a first detent 2264 and a second detent 2266 spaced apart from the first detent 2264. As this lock 2208 is small and compact, less material is used which results in a reduction in cost and packaging space.

Figure 25:
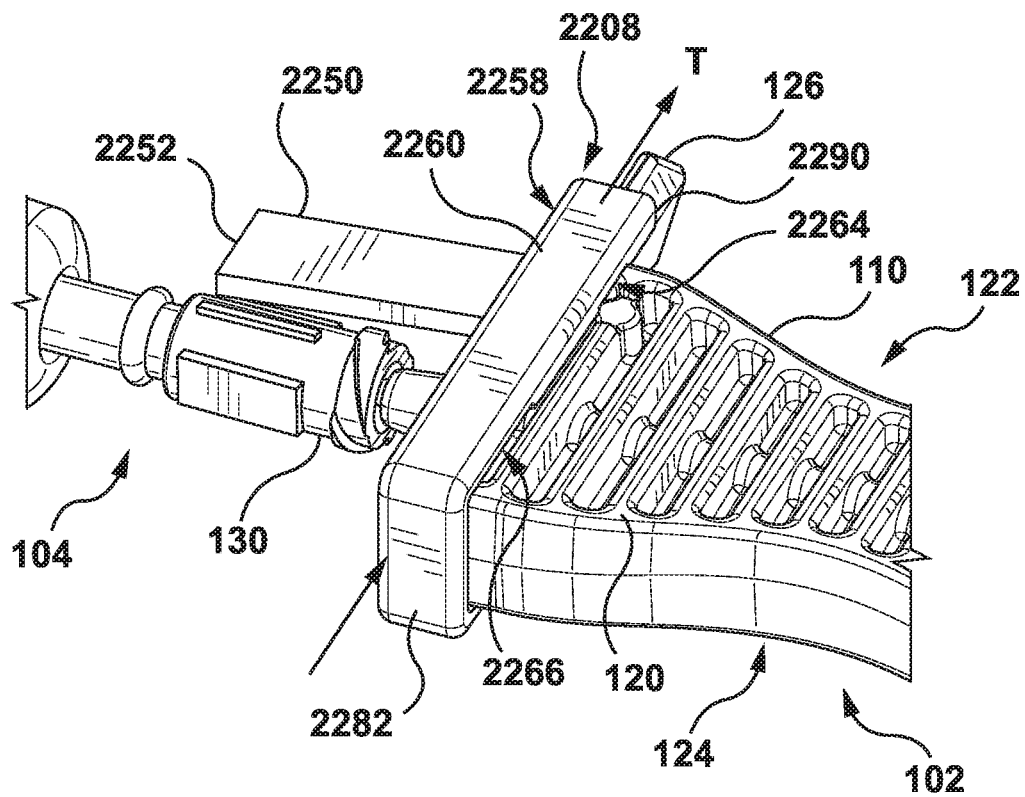
FIG. 25 a partial perspective view of the system for transseptal perforation, showing a needle of the system in an in-use position, and including the lock of FIG. 22 to 24.

Referring now to FIGS. 23 to 25, the system 100 is shown with the lock 2208. The lock 2208 can be used to prevent advancement of the needle 112 from the shrouded position (shown in FIG. 24) to the in-use position (shown in FIG. 25), until such advancement is desired by the operator. For example, the lock 2208 can be used up until the operator of the system is ready to perforate a target location within a patient's heart, for example during advancement of the dilator 104 and transseptal perforation device 102 through the sheath (shown in FIGS. 1 and 2) towards the target location, and during any preliminary tests, in order to prevent inadvertent contact between the perforating tip (shown in FIGS. 1 and 2) and non-target locations within a patient's body, and prevent inadvertent damage to such non-target locations.

During use, the clip 2258 can snap onto the handle 110 of the transseptal perforation device 102, to position the spacer 2250 proximal of the dilator hub 130, and between the dilator hub 130 and the handle 110, so that if advancement of the needle 112 beyond the shrouded position is attempted (e.g. inadvertently), the spacer 2250 will abut the dilator hub 130 to prevent movement of the needle 112 to the in-use position by preventing movement of the handle 110 towards the dilator hub 130. More specifically, referring to FIG. 24, the lock 2208 is shown with the spacer 2250 in a lock position. In the lock position, the spacer 2250 is proximal of the dilator hub 130, and between the dilator hub 130 and the handle 110, to abut the dilator hub 130 if movement of the handle 110 towards the dilator hub 130 is attempted. This abutment, provided by the first abutment surface 2252 (visible in FIG. 23) prevents movement of the needle 112 to the in-use position, by preventing movement of the handle 110 towards the dilator hub 130.

Referring to FIG. 25, the lock 2208 is shown with the spacer 2250 in an unlock position. In the unlock position, the spacer 2250 is moved radially away from the dilator hub 130 and the handle 110, in a direction T transverse to the longitudinal axis of the spacer 2250, so that the spacer 2250 is clear of the dilator hub 130, to allow movement of the handle 110 towards the dilator hub 130 and therefore allow movement of the needle 112 to the in-use position.

Referring still to FIGS. 24 and 25, the clip 2258 serves to secure the lock 2208 to the transseptal perforation device. In the embodiment shown, the clip 2258 secures the lock 2208 to the handle 110 with the spacer 2250 in the lock position, and to secures the lock 2208 to the handle 110 with the spacer in the unlock position, and allows for movement of the spacer 2250 between the lock and unlock positions. That is, the clip 2258 is removably securable to the handle 110 in a first position, shown in FIG. 24, to secure the spacer 150 in the locked position, and removably securable to the handle 110 in a second position, shown in FIG. 25 to secure the spacer 2250 in the unlock position. The lock 2208 can remain in either the locked or unlocked positions such that it may be used multiple times throughout the procedure.

More specifically, the slot 2262 (shown in FIG. 22) of the clip 2258 can receive the handle 110, particularly the front section 126 (shown in FIGS. 23 to 25) of the outer rib 120 of the handle 110, which can slide into the slot 2262 going in a direction T transverse to the longitudinal axis of the spacer 2250 (as illustrated in FIG. 25), from the lower section 124 of the outer rib 120 towards the upper section 122 of the outer rib 120. Alternatively, the lock 2208 may be positioned in the opposite configuration. The clip 2258 can receive the front section 126 of the outer rib 120 of the handle 110, sliding into the slot 2262 in the opposite direction, moving from the upper section 122 of the outer rib 120 towards the lower section 124 of the outer rib 120.

As the front section 126 of the handle 110 is inserted into the slot 2262, the outer rib 120 of the upper section 122 engages with the outer edge 2290 (visible in FIG. 22). The lower section 124 will engage the second detent 2266 by snapping into the second detent 2266 (as seen in FIG. 24). When the lower section 124 is engaged with the second detent 2266, the spacer 150 is secured in the locked position, as shown in FIG. 24. If further force is applied to the bottom face 2282 of the lock 2280, the clip 2258 slides along the front section 126 which moves further into the slot 2262. The lower section 124 will snap out of engagement with the second detent 2266. The outer rib 120 of the upper section 122 then engages with the first detent 2264 by snapping into the first detent 2264 (as seen in FIG. 25). When the outer rib 120 of the upper section 122 is engaged with the first detent 2264, the spacer 2250 is secured in the unlock position, as shown in FIG. 25. Accordingly, the spacer 2250 can move from the lock and unlock position by sliding the clip 2258 into and out of engagements with the first 2264 and second detent 2266. The configuration of the clip 2258 can advantageously allow for one-handed operation of the lock 2208 throughout the procedure.

An example method of using the lock 2208 and system 100 of FIGS. 22 to 25 will now be described. In use, the sheath 106 and dilator 104 (seen in FIG. 1) can be advanced to the right atrium of a patient's heart via the femoral vein and the dilating tip 138 can be positioned adjacent a target location in the right atrium, for example the fossa ovalis of the atrial septum. Prior to or after advancement of the sheath 106 and dilator 104, the lock 2208 can be secured to the transseptal perforation device 102, and the spacer 2250 of the lock 2208 can be positioned the lock position, as shown in FIG. 24. More specifically, the clip 2258 can be engaged with the handle 110 of the transseptal perforation device 102, by sliding the front section 126 into the slot 2262, and engaging the second detent 2266 with the lower section 124, to secure the lock 2208 to the transseptal perforation device 102 with the spacer 2250 in a lock position. With the spacer 2250 in the lock position, the transseptal perforation device 102 can be advanced into the dilator 104. As described above, in the lock position, the spacer 2250 is positioned between the dilator hub 130 and the handle 110 of the transseptal perforation device 102, to abut the dilator hub 130 and the handle 110 and limit advancement of the transseptal perforation device 102 into the dilator 104, and thereby prevent advancement of a perforating tip 118 of the transseptal perforation device 102 proud of a dilating tip 138 of the dilator 104, to the in-use position. With the perforating tip 118 shrouded in the dilator 104 and prevented from advancing to the in-use position by the lock 2208, various optional procedures can be carried out, including procedures to confirm the position of the dilating tip 138 (e.g. using fluoroscopy).

When the operator of the system 100 is ready, the spacer 2250 can be removed from the lock position, to clear the spacer 150 of the dilator hub 130. That is, the spacer 2250 can be moved from the lock position to the unlock position, by applying force to the bottom face 2282 which will move the lock 2208 along the front section 126 of the handle 110. This will result in the second detent 2266 out of engagement with the lower section 124, sliding the clip 2258 along the front section 126 of the handle 110. The first detent 2264 then snaps into engagement with the outer rib 120 of the upper section 122 (as shown in FIG. 25), causing the spacer 2250 to move into the unlock position. The transseptal perforation device 102 can then be advanced further into the dilator 104 to position the perforating tip 118 proud of the dilating tip 138, in the in-use position. The perforating tip 118 can then be used to perforate the target anatomy.

Referring now to FIGS. 10 to 16, another example lock is shown. The lock 1008 of FIGS. 10 to 16 is similar to the lock of FIGS. 3 to 9, and features of the lock 1008 that are like features of the lock 108 will be referred to with like reference numerals, incremented by 900.

The lock 1008 includes a spacer 1050 and a clip 1058 that are similar to the spacer 150 and clip 158 of FIGS. 10 to 16; however, the lock 1008 further includes a rotary stop 1068 for releasably fixing the rotational position of the transseptal perforation device 102 with respect to the dilator 104. That is, referring back to FIGS. 1 and 2, the sheath 106 includes a curved region 170 (also referred to herein as a 'sheath curved region'), which is shaped to allow the dilating tip 138 to reach the heart when advanced towards the heart from the femoral vein. Similarly, the dilator 104 includes a curved region (also referred to herein as a 'dilator curved region'), and the needle includes a curved region (also referred to as a 'needle curved region'). The dilator curved region and needle curved region are within the sheath curved region 170 in FIGS. 1 and 2, and are not visible.

In order to position the dilating tip 138 of the dilator 104 and the perforating tip 118 of the needle 112 adjacent the target location, the dilator 104 and needle 112 are generally positioned within the sheath 106 with the dilator curved region, needle curved region, and sheath curved region 170 generally curved in the same direction, as shown in FIGS. 1 and 2 (i.e. curved upwardly in FIGS. 1 and 2, as opposed to downwardly). However, due to the flexibility of the needle 112, it is possible to inadvertently advance the needle 112 through the dilator 104 and sheath 106 with the needle curved region curved in a different direction from the dilator curved region and sheath curved region 170 (e.g. with the needle 112 rotated about it's longitudinal axis by 180 degrees, so that it is curved downwardly). In such instances, when the perforating tip 118 is advanced from the dilator 104, it can curve away from the target location. In the example of FIGS. 10 to 16, the rotary stop 1068 of the lock 1008 can be used to avoid or prevent or mitigate this issue, by fixing the rotational position of the transseptal perforation device 102 with respect to the sheath 106 with the needle curved region curved in the same direction as the sheath curved region 170.

Referring to FIGS. 10 to 14, in the example shown, the rotary stop 1068 includes a pair of arms 1072, 1074. The arms 1072, 1074 are generally parallel to the spacer 1050, are offset from the longitudinal axis 1056 of the spacer 1050, and extend distally beyond the first abutment surface 1052 of the spacer 1050. The arms 1072, 1074 define a space 1076 therebetween for receiving the fluid port 142 of the sheath hub 140. When the fluid port 142 of the sheath hub 140 is received in the space 1076, or simply when the space 1076 is aligned to receive the fluid port 142 of the sheath hub 140, the curved region of the needle is curved in the same direction as the curved region 170 of the sheath 106. That is, engagement of the rotary stop 1068 of the lock 1008 with the sheath hub 140 fixes the rotational position of the transseptal perforation device 102 with respect to the sheath 106. In an alternative embodiment, a curve indicator (not shown) may be present, replacing the fluid port 142. The curve indicator may comprise an arm extending from the hub of the sheath hub 140, wherein the curve indicator denoting the direction of the curved region. The curve indicator may then be received in the space 1076 between the arms 1072, 1074; this engagement of the rotary stop 1068 of the lock 1008 with the curve indicator of the sheath hub 140 fixes the rotational position of the transseptal perforation device 102 with respect to the sheath 106.

Referring to FIG. 15, in use, as the needle 112 (not visible in FIG. 15) is advanced into the sheath 106 with the spacer 1050 in the lock position, the handle 110 of the transseptal perforation device 102 can be rotated to align the space 1076 with the fluid port 142, so that the fluid port 142 is received in the space 1076. When the operator is ready, the spacer 1050 can be moved to the unlock position, and the handle can be advanced to move the transseptal perforation device 102 to the in-use position, as shown in FIG. 16. As the transseptal perforation device 102 is moved to the in-use position, the fluid port 142 is slid further into the space 1076 between the arms 1072, 1074. That is, the engagement of the rotary stop 1068 and the sheath hub 140 is maintained during advancement of the transseptal perforation device 102 to the in-use position, as well as during use of the transseptal perforation device 102. The engagement of the fluid port 142 and the arms 1072, 1074 fixes the rotational position of the transseptal perforation device 102 with respect to the sheath 106, and prevents rotation of the transseptal perforation device 102 about its longitudinal axis, which ensures that the curved region of the needle is curved in the same direction as the curved region 170 of the sheath 104 (or facilitates curving of the curved region of the needle in the same direction as the curved region 170 of the sheath 104). A similar method may be used for the embodiment where a curve indicator is used instead of a fluid port 142.

Referring now to FIGS. 17 to 21, another example lock is shown. Features of the lock 1708 that are like features of the lock 108 will be referred to with like reference numerals, incremented by 1600.

Figure 17:
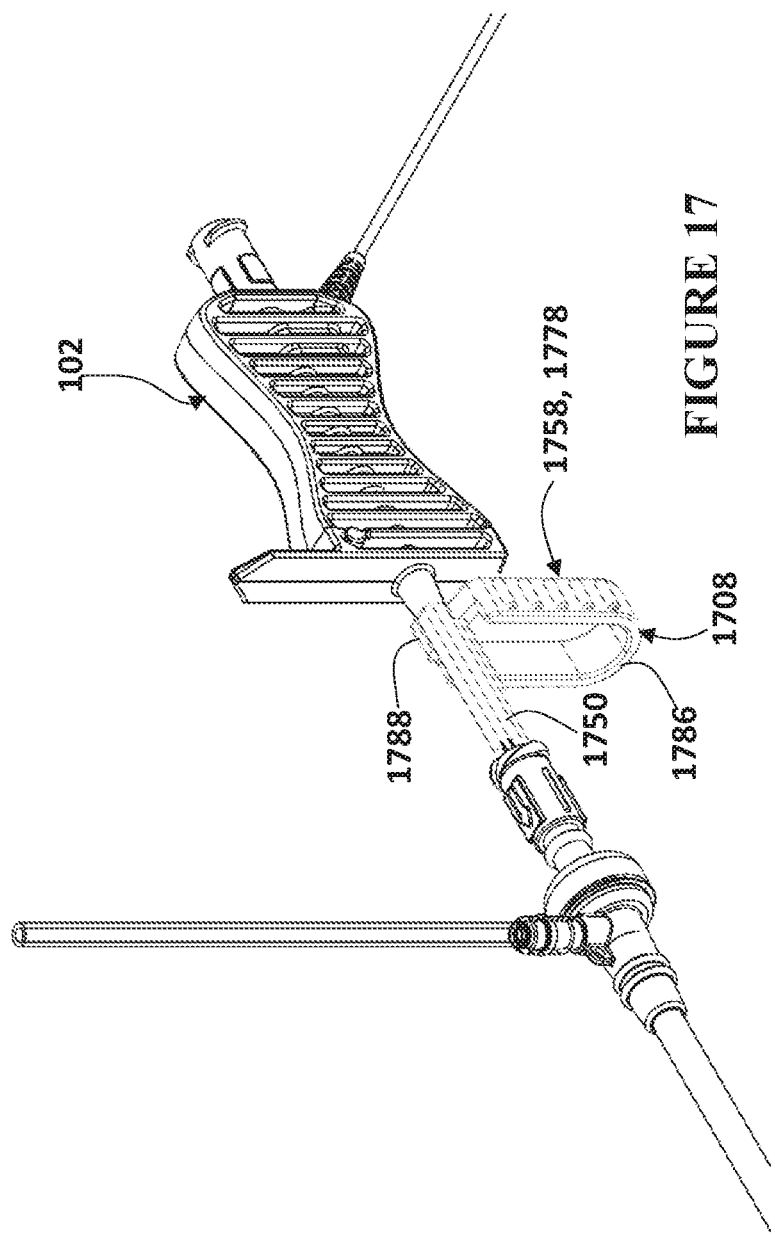
FIG. 17 is a partial perspective view of another system for transseptal perforation, with a needle of the system in a shrouded position, and including another example lock.

In the lock 1708, the spacer 1750 is similar to the spacer of FIGS. 3 to 9; however, the clip 1758 is in the form of a clamp 1778 that can be releasably secured to the needle proximal end 114 of the transseptal perforation device 102, as shown in FIG. 17 (the needle 112 is not visible in FIG. 17). Specifically, referring to FIGS. 18 to 21, the spacer 1750 includes a first side 1780 and a second side 1782, and the first side includes a groove 1784 (labelled only in FIGS. 18, 19, and 20) for receiving a portion of the needle 112. The clamp 1778 includes an arm 1786 that is generally U-shaped and resiliently flexible, and that extends from the spacer 1750 generally downwardly, laterally in a first direction, back upwardly, and laterally in a second direction opposite the first direction. A head 1788 is at the end of the arm 1786, and is positioned proximate the first side 1780 of the spacer 1750. The clamp 1778 is biased towards a clamped state, shown in FIGS. 20 and 21, in which due to the resiliency of the arm 1786, the head 1788 presses against the first side 1780 of the spacer 1750. The clamp 1778 is movable to a released state, shown in FIGS. 18 and 19, by squeezing or forcing the sides of the arm laterally towards each other (as shown by the arrows in FIG. 21), to move the head 1788 away from the first side of the spacer 1750. In use, as shown in FIG. 17, the spacer 1750 can be secured in the lock position by clamping the needle 112 between the head 1788 and the spacer 1750. To remove the spacer 1750 from the lock position, the clamp 1778 can be squeezed and the lock 1708 can be removed from the transseptal perforation device 102.

In any of the above examples, the system can include a sensor for detecting when the spacer is in the lock position. Optionally, the sensor can be used to detect when the spacer is in the lock position, and energizing of the transseptal perforation device can be automatically prevented when the sensor detects that the spacer is in the lock position.

In any of the above examples, the parts of the system can be provided separately, or can be provided together as a kit of parts.

In the above examples, the locks are described with respect to a transseptal perforation system. In alternative examples, the locks may be used with other medical devices and for other purposes, for example for positioning a first medical device with respect to a second medical device. In such examples, instead of engaging with a handle and needle of a transseptal perforation device and with a hub of a dilator or sheath, the lock may engage with various parts or portions of the first and second medical devices. In one particular example, instead of a transseptal perforation device including handle and a needle, a simple guidewire could be used for transseptal perforation (e.g. a guidewire in which the wire serves as the needle, and which lacks a handle or other structure at its proximal end) with a dilator and optionally a sheath. In such instances, a lock (e.g. lock 1708) could clamp directly onto the guidewire at a desired position (i.e. a position proximal of the dilator hub, to abut the dilator hub as the guidewire is advanced through the dilator).

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A kit of parts for a system for transseptal perforation, the kit of parts comprising:
   a first medical device comprising a first medical device proximal end and a first medical device distal tip;
   a second medical device comprising a second medical device proximal end and a second medical device distal tip, wherein the second medical device proximal end comprises a hub;
   the first medical device is receivable and advanceable within the second medical device such that the first medical device may be advanced to a shrouded position in which the first medical device distal tip is shrouded within the second medical device;
   the first medical device may be advanced to an in-use position in which the first medical device distal tip is proud of the second medical device distal tip;
   a lock for releasably preventing advancement of the first medical device from the shrouded position to the in-use position;
   the lock comprising an elongate spacer positionable in a lock position proximal of the second medical device hub to abut the second medical device hub and prevent advancement of the first medical device to the in-use position; and,
   a clip for securing the lock to the first medical device.

2. The kit of parts of claim 1, wherein the first medical device comprises a transseptal perforation device, wherein the transseptal perforation devices includes an elongate needle, and the second medical device comprises a dilator, wherein the dilator includes a dilator hub and an elongate dilator body.

3. The kit of parts of claim 2, wherein:
   the transseptal perforation device comprises a handle, and the needle proximal end is secured to the handle;
   in the shrouded position, the handle is spaced from the dilator hub, and in the in-use position, the handle is moved towards the dilator hub; and
   in the lock position, the spacer is positioned between the dilator hub and the handle to abut the dilator hub and the handle such that there is a minimum space between the dilator hub and handle.

4. The kit of parts of claim 3, wherein the spacer is movable from the lock position to an unlock position, wherein in the unlock position, the spacer is moved clear of the dilator hub to allow movement of the handle towards the dilator hub and allow movement of the needle to the in-use position, and wherein the spacer is securable in the unlock position by the clip.

5. The kit of parts of claim 4, wherein the clip comprises a tongue extending orthogonally from the spacer and defining a slot for receiving at least a portion of the handle.

6. The kit of parts of claim 5, wherein:
the handle comprises a rib; and
the tongue comprises a first detent engageable with the rib to maintain the spacer in the unlock position, and a second detent spaced from the first detent and engageable with the rib to maintain the spacer in the lock position.

7. The kit of parts of claim 2, wherein the kit further comprises a sheath having a sheath hub including a radially extending fluid port, an elongate sheath body extending longitudinally from the sheath hub and having a sheath body proximal end adjacent the sheath hub and a sheath body distal end spaced from the sheath hub, wherein a sheath lumen extends longitudinally through the sheath from the sheath hub to the sheath body distal end, and wherein the dilator body is advanceable through the sheath lumen to position the dilator body within the sheath body with the dilator hub adjacent the sheath hub and the dilating tip proud of the sheath body distal end.

8. The kit of parts of claim 7, wherein the clip further comprises a rotary stop for releasably fixing the rotational position of the transseptal perforation device with respect to the sheath, the rotary stop including a pair of arms defining a space therebetween for receiving a curve indicator.

9. The kit of parts of claim 8, wherein the curve indicator comprises a fluid port.

10. The kit of parts of claim 1, wherein the clip is slidable in a direction transverse to a longitudinal axis of the spacer, to move the spacer between the lock position and the unlock position.

11. The kit of parts of claim 1, wherein the lock further comprises a rotary stop for fixing the rotational position of the first medical device.

12. The kit of parts of claim 11, wherein the rotary stop fixes the rotational position of the first medical device relative to the second medical device.

13. The kit of parts of claim 1, further comprising a sensor for detecting when the spacer is in the lock position.

14. A lock for positioning a first medical device with respect to a second medical device, the lock comprising:
a spacer for allowing partial advancement of the first medical device towards the second medical device, the spacer being elongate and having a first abutment surface and a second abutment surface spaced apart along a longitudinal axis of the spacer, wherein the spacer is movable between a lock position and an unlock position, wherein in the lock position the spacer is moved transverse to the longitudinal axis with respect to the unlock position; and
a clip integral with the spacer and removably securable to the first medical device in a first position to secure the spacer in the unlock position, and removably securable to the first medical device in a second position to secure the spacer in the lock position, wherein the clip comprises a tongue extending orthogonally from the spacer and defining a slot for receiving a portion of the first medical device, and the tongue comprises a first detent engageable with the portion of the first medical device to secure the spacer in the unlock position, and a second detent spaced from the first detent and engageable with the portion of the first medical device to maintain the spacer in the lock position.

15. The lock of claim 14, wherein the clip is slidable transverse to the longitudinal axis between the first position and the second position.

16. The lock of claim 14, further comprising a rotary stop integral with the spacer for fixing the rotational position of the first medical device with respect to the second medical device, the rotary stop comprising a pair of arms offset from the longitudinal axis and defining a space therebetween for receiving a portion of the second medical device.

17. The lock of claim 16, wherein the arms extend distally beyond the first abutment surface of the spacer.

18. The lock of claim 17, wherein the arms are positioned to receive the portion of the second medical device when the spacer is in the lock position and when the spacer is in the unlock position.

19. A kit of parts for a system for transseptal perforation, the kit of parts comprising:
a transseptal perforation device including an elongate needle, the needle having a needle proximal end and a needle distal end including a perforating tip;
a dilator including a dilator hub and an elongate dilator body having a dilator lumen extending therethrough, the dilator body having a dilator body proximal end secured to the dilator hub and a dilator body distal end including a dilating tip, wherein the needle is advanceable through the dilator from the dilator hub towards the dilating tip to a shrouded position in which the perforating tip is shrouded within the dilator, and to an in-use position in which the perforating tip is proud of the dilating tip; and
a lock for releasably preventing advancement of the needle from the shrouded position to the in-use position, the lock comprising an elongate spacer positionable in a lock position proximal of the dilator hub to abut the dilator hub and prevent movement of the needle to the in-use position, and a clip for securing the lock to the transseptal perforation device with the spacer in the lock position.

* * * * *